United States Patent
Ertl et al.

(10) Patent No.: US 9,624,510 B2
(45) Date of Patent: Apr. 18, 2017

(54) ADENOVIRAL VECTORS COMPRISING PARTIAL DELETIONS OF E3

(71) Applicant: The Wistar Institute, Philadelpia, PA (US)

(72) Inventors: Hildegund C. J. Ertl, Villanova, PA (US); Xiang Yang Zhou, North Wales, PA (US)

(73) Assignee: The Wistar Institute, Philadelphia, PA (US)

(*) Notice: Subject to any disclaimer, the term of this patent is extended or adjusted under 35 U.S.C. 154(b) by 0 days.

(21) Appl. No.: 14/190,787

(22) Filed: Feb. 26, 2014

(65) Prior Publication Data
US 2014/0248305 A1 Sep. 4, 2014

Related U.S. Application Data

(60) Provisional application No. 61/771,370, filed on Mar. 1, 2013.

(51) Int. Cl.
*C12N 15/86* (2006.01)
*C12N 15/861* (2006.01)

(52) U.S. Cl.
CPC .......... *C12N 15/86* (2013.01); *C12N 15/861* (2013.01); *C12N 2710/10043* (2013.01)

(58) Field of Classification Search
None
See application file for complete search history.

(56) References Cited

U.S. PATENT DOCUMENTS

2004/0253210 A1* 12/2004 Robert-Guroff ....... A61K 39/00 424/93.2
2005/0095270 A1* 5/2005 Staecker ............... A61K 38/06 424/437

OTHER PUBLICATIONS

Tatsis et al., The Journal of Immunology, 2009, 182:6587-6599.*
He et al., Proc. Natl. Acad. Sci. USA, 1998, 95:2509-2514.*
Horwitz, The Journal of Gene Medicine, 2004, 6:S172-S183.*
Chen et al., Journal of Virology, 2010, 84(20):10522-10532.*
Bayer et al., Retrovirology, 2011, 8:75.*
Cervasi et al., Journal of Virology, Sep. 2013, 87(17);9420-9430.*
Shiver et al., "Replication-incompetent adenoviral vaccine vector elicits effective anti-immunodeficiency-virus immunity." 2002, Nature 415:331-335.
Casimiro, et al., "Comparative Immunogenicity in Rhesus Monkeys of DNA Plasmid, Recombinant Vaccinia Virus, and Replication-Defective Adenovirus Vectors Expressing a Human Immunodeficiency Virus Type 1 gag Gene." 2003, J Virol 77(11):6305-5313.
Lichtenstein et al., "Functions and mechanisms of action of the adenovirus E3 proteins." 2004, International Reviews of Immunology 23: 75-111.
Casimiro et al., "Attenuation of simian immunodeficiency virus SIVmac239 infection by prophylactic immunization with DNA and recombinant adenoviral vaccine vectors expressing Gag." 2005, J Virol 79(24):15547-15555.
Tatsis et al., "Chimpanzee-origin adenovirus vectors as vaccine." 2006, Gene Therapy 13:421-429.
Xiang et al., "Chimpanzee Adenovirus Antibodies in Humans, Sub-Saharan Africa." 2006, Emerging Infectious Diseases 12(10):1596-1599.
Engram et al., "Vaccine-induced, simian immunodeficiency virus-specific CD8+ T cells reduce virus replication but do not protect from simian immunodeficiency virus disease progression." 2009, J Immunol 183:706-717.

* cited by examiner

*Primary Examiner* — Nicole Kinsey White
(74) *Attorney, Agent, or Firm* — Saul Ewing LLP; Kathryn Doyle

(57) ABSTRACT

This disclosure provides replication-incompetent adenoviral vectors useful in vaccine development and gene therapy. The disclosed vectors comprise a selective deletion of E3 and are particularly useful for preparation of vaccines development and for gene therapy using toxic transgene products that result in vector instability that occurs when the entire E3 domain is deleted.

13 Claims, No Drawings

ADENOVIRAL VECTORS COMPRISING PARTIAL DELETIONS OF E3

CROSS-REFERENCE TO RELATED APPLICATION

This application claims priority under 35 U.S.C. §119(e) to U.S. Provisional Patent Application No. 61/771,370, filed on Mar. 1, 2013, and is hereby incorporated herein by reference in its entirety.

STATEMENT REGARDING FEDERALLY SPONSORED RESEARCH OR DEVELOPMENT

This invention was made with government support under NIH Grant Nos. P01 AI082282 and U19AI074078, awarded by National Institutes of Health. The government has certain rights in the invention.

TECHNICAL FIELD

This disclosure relates generally to adenoviral vectors.

DETAILED DESCRIPTION

This disclosure provides replication-incompetent adenoviral vectors useful in vaccine development and gene therapy. These vectors comprise a selective deletion of the viral genomic region E3 but retain anti-apoptotic function otherwise provided by E3-encoded proteins. This is achieved either by retaining portions of E3 or by including in the vector open reading frames (ORFs) that encode anti-apoptotic proteins. The disclosed vectors are particularly useful for vaccine development and for gene therapy in which the encoded protein products are toxic and result in vector instability.

In some embodiments, a replication-incompetent adenovirus vector comprises a deletion of E3 ORF3, ORF4, ORF5, ORF6, and ORF7; and comprises at least one open reading frame encoding an anti-apoptotic protein. The anti-apoptotic protein can be a native protein of the adenovirus, such as the proteins encoded by ORF8 or ORF9, or can be an apoptotic protein from a different source, e.g., a p53 inhibitor, Bcl-$X_L$, BCL2, BCL2L1, BCL2A1, BAG1, TRAF1, BIRC3, BIRC5, BAK1, cIAP1, c-IAP2, XIAP, or API5. These proteins and nucleotide sequences encoding them are well known in the art. A replication-incompetent adenovirus vector can comprise one open reading frame encoding an anti-apoptotic protein or can comprise several such open reading frames (e.g., 2, 3, 4).

An adenovirus vector can be rendered replication-incompetent by various means, including, but not limited to, a complete deletion of E1 or a functional deletion of E1 (i.e., a deletion of less than the entire E1a and E1b loci, but sufficient to disable the function of the E1 genes, and mutations at functional sites).

The disclosed vectors can be generated using basic cloning techniques and can be used thereafter to express a variety of different protein products.

In some embodiments, the serotype of the replication-incompetent adenovirus vector is a human serotype (e.g., a serotype of group A, group B, group C, group D, group E, group F). Human serotypes include, but are not limited to, Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, and Ad50.

In other embodiments, the serotype of the replication-incompetent adenovirus vector is a chimpanzee serotype (e.g., Ad C1, Ad C3, Ad C6, Ad C7, Ad C68).

Replication-incompetent adenovirus vectors disclosed herein are particularly useful when an antigenic protein is toxic to cell machinery upon expression by the vector. For example, the disclosed replication-incompetent adenovirus vectors carrying a coding sequence for HIVgp140 can be readily rescued, express the gp140 protein, and remain stable after 12 serial passages.

Accordingly, in some embodiments, the antigenic protein is all or an antigenic portion of an HIV-1 envelope protein. In some embodiments, the antigenic protein is all or an antigenic portion of an HCV envelope protein. In some embodiments, the antigenic protein is all or an antigenic portion of a protein of *M. tuberculosis*. In some embodiments, the antigenic protein is all or an antigenic portion of a protein of *Plasmodium* (e.g., *P. falciparum*).

In some embodiments, the antigenic protein is all or an antigenic portion of a protein of an infectious eukaryotic organism, such as a *Plasmodium* (e.g., *Plasmodium falciparum*, *Plasmodium vivax*, *Plasmodium ovale*, *Plasmodium malariae Plasmodium diarrhea*), and fungi such as *Candida* (e.g., *Candida albicans*), *Aspergillus* (e.g., *Aspergillus fumigatus*), *Cryptococcus* (e.g., *Cryptococcus neoformans*), *Histoplasma* (e.g., *Histoplasma capsulatum*), *Pneumocystis* (e.g., *Pneumocystis jirovecii*), and *Coccidioides* (e.g., *Coccidioides immitis*).

In some embodiments, the antigenic protein is all or an antigenic portion of a protein of an infectious virus, such as an influenza virus, retrovirus (e.g., HIV, Rous Sarcoma Virus (RSV), human endogenous retrovirus K (HERV-K)), human endogenous retrovirus K (HERV-K), papillomavirus (e.g., human papilloma virus), picornavirus (e.g., Hepatitis A, Poliovirus), hepadnavirus (e.g., Hepatitis B), flavivirus (e.g., Hepatitis C, Yellow Fever virus, Dengue Fever virus, Japanese encephalitis virus, West Nile virus), togavirus (e.g., chikungunya virus, Eastern equine encephalitis (EEE) virus, Western equine encephalitis (WEE) virus, Venezuelan equine encephalitis (VEE) virus,), herpesvirus (e.g., Cytomegalovirus), paramyxovirus (Parainfluenza virus, Pneumonia virus, Bronchiolitis virus, common cold virus, Measles virus, Mumps virus), rhabdovirus (e.g., Rabies virus), Filovirus (e.g., Ebola virus), bunyavirus (e.g., Hantavirus, Rift Valley Fever virus), calicivirus (e.g., Norovirus), or reovirus (e.g., Rotavirus, Epstein-Barr virus, Herpes simplex virus types 1 & 2).

In some embodiments, the antigenic protein is all or an antigenic portion of a protein of an infectious gram-negative bacterium or gram-positive bacterium, *Bacillus* (e.g., *Bacillus anthracis*), *Mycobacterium* (e.g., *Mycobacterium tuberculosis*, *Mycobacterium Leprae*), *Shigella* (e.g., *Shigella sonnei*, *Shigella dysenteriae*, *Shigella flexneri*), *Helicobacter* (e.g., *Helicobacter pylori*), *Salmonella* (e.g., *Salmonella enterica*, *Salmonella typhi*, *Salmonella typhimurium*), *Neisseria* (e.g., *Neisseria gonorrhoeae*, *Neisseria meningitidis*), *Moraxella* (e.g., *Moraxella catarrhalis*), *Haemophilus* (e.g., *Haemophilus influenzae*), *Klebsiella* (e.g., *Klebsiella pneumoniae*), *Legionella* (e.g., *Legionella pneumophila*), *Pseudomonas* (e.g., *Pseudomonas aeruginosa*), *Acinetobacter* (e.g., *Acinetobacter baumannii*), *Listeria* (e.g., *Listeria monocytogenes*), *Staphylococcus* (e.g., methicillin-resistant, multidrug-resistant, or oxacillin-resistant *Staphylococcus aureus*), *Streptococcus* (e.g., *Streptococcus pneumoniae*, *Streptococcus pyogenes*, *Streptococcus agalactiae*), *Corynebacterium* (e.g., *Corynebacterium diphtheria*), *Clostridium* (e.g., *Clostridium botulinum*, *Clostridium* tetani, Clostridium difficile), Chlamydia (e.g., Chlamydia pneumonia, Chlamydia trachomatis), Camphylobacter (e.g., Camphylobacter jejuni), Bordetella (e.g., Bordetella pertussis), Enterococcus (e.g., Enterococcus faecalis, Enterococcus faecum, Vancomycin-resistant enterococcus (VRE)), Vibrio (e.g., Vibrio cholerae), Yersinia (e.g., Yersinia pestis), Burkholderia (e.g., Burkholderia cepacia complex), Coxiella (e.g., Coxiella burnetti), Francisella (e.g., Francisella tularensis), and Escherichia (e.g., enterotoxigenic, enterohemorrhagic or Shiga toxin-producing E. coli, such as ETEC, EHEC, EPEC, EIEC, EAEC)).

Production, purification and quality control procedures for Ad vectors are well established.[17] Once a vector backbone is created, molecular cloning can be used to create an adenoviral plasmid comprising a coding sequence for an antigenic protein ("transgene"). The plasmid can be transfected into packaging cells that provide E1 of a suitable adenovirus serotype in trans. Packaging cells are well known in the art, and cells lines such as HEK293 can be used for this purpose. Viral particles are then harvested once plaques become visible. Fresh cells can then be infected to ensure continued replication of the adenovirus. Quality can be assessed using Southern blotting or other methods, such as restriction enzyme mapping, sequences, and PCR, to confirm the presence of the transgene and the lack of gene rearrangements or undesired deletions.

Vaccine compositions comprising adenovirus particles made using replication-incompetent adenovirus vectors disclosed herein can be used to induce immunity against the encoded antigenic protein.

Vaccines can be formulated using standard techniques and can comprise, in addition to a replication-incompetent adenovirus vector encoding a desired protein, a pharmaceutically acceptable vehicle, such as phosphate-buffered saline (PBS) or other buffers, as well as other components such as antibacterial and antifungal agents, isotonic and absorption delaying agents, adjuvants, and the like. In some embodiments vaccine compositions are administered in combination with one or more other vaccines.

Dosage units of vaccine compositions can be provided. Such dosage units typically comprise $10^8$ to $10^{11}$ adenoviral particles (e.g., $10^8$, $5 \times 10^8$, $10^9$, $5 \times 10^9$, $10^{10}$, $5 \times 10^{10}$, $10^{11}$, $10^8$ to $10^9$, $10^8$ to $10^{10}$, $10^9$ to $10^{10}$, $10^9$ to $10^{11}$, $5 \times 10^8$ to $10^9$, $5 \times 10^8$ to $10^{10}$, $5 \times 10^9$ to $10^{10}$, $5 \times 10^9$ to $10^{11}$, $10^8$ to $5 \times 10^9$, $10^8$ to $5 \times 10^{10}$, $10^9$ to $5 \times 10^{10}$, $10^9$ to $10^{11}$, $5 \times 10^8$ to $5 \times 10^9$, $5 \times 10^8$ to $5 \times 10^{10}$, $5 \times 10^9$ to $5 \times 10^{10}$, $5 \times 10^9$ to $10^{11}$).

Immune responses against one or more encoded proteins or antigenic portions thereof can be induced using the disclosed vaccine compositions or dosage units. Methods of administration include, but are not limited to, mucosal (e.g., intranasal), intraperitoneal, intramuscular, intravenous, and oral administration. Immune responses can be assessed using suitable methods known in the art, as disclosed, for example, in WO2012/02483.

Those skilled in the art will appreciate that there are numerous variations and permutations of the above described embodiments that fall within the scope of the appended claims.

EXAMPLE 1

Construction of pAdC6 020

The E3 region of AdC6 contains 5052 base pairs (bp), with a total of nine open reading frames: ORF1 is 325 bp; ORF2 is 624 bp; ORF3 is 531 bp; ORF4 is 684 bp; ORF5 is 612 bp; ORF6 is 867 bp; ORF7 is 276 bp; ORF8 is 435 bp; and ORF9 is 408 bp. ORF3, ORF4, ORF5, ORF6 and ORF7 were deleted to create the vector "AdC6 020" (the total length of the deleted sequence was 3218 bp).

EXAMPLE 2

Construction of Stable Adenoviral Vectors Comprising HIV Envelope Sequences pAdC6 020 was used to create two vectors encoding HIV envelope sequences, "AdC6 020-HIVgp140-DU172" and "AdC6 020-HIVgp140-DU422." The HIV strains that served as donors for the envelope sequences were isolated from clinical materials. The coding sequences were codon-optimized to permit enhanced expression in human cells. To create the pAdC6 020 plasmid, PCR-based cloning strategies were used to obtain the fragment without ORF3, ORF4, ORF5, ORF6 and ORF7 of E3 region. By using that PCR product, the pXY-E3 deleted plasmid was generated. Both pXY-E3 deleted (donor for insert) and pC6 E3 deleted (donor for backbone) plasmids were digested with PspX I and Nco I restriction enzymes to result in the pC6 E3 modified plasmid. Finally the modified E3 fragment was excised out from pC6 E3 modified plasmid by Sbf I digestion and cloned into pAdC6 000-eGFP plasmid (E1 deleted only) with E3 removed by Sbf I digestion. This resulted in pAdC6 020-eGFP. AdC6 vectors comprising the HIV coding sequences and a deletion of E1 or a deletion of E1 and of all the ORFs of E3 could not be rescued. Similar problems were encountered using adenovirus vectors of human serotype 5 (Ad5) and 26 (Ad26). Upon modifying the E3 deletion within AdC6, Ad5 and Ad26, however, all of those vectors could readily be rescued. These vectors passed quality control assays including restriction enzyme mapping, and Western blots showed that vectors expressed HIV-1 gp140 upon transfection of cells. These vectors were stable after 12 sequential passages shown by restriction enzyme mapping. Vectors rescued successfully by modified E3 region are summarized in the following table.

| Vector Name | Rescued | Viral Stability | Western Blot for transgene | Viral Genome |
|---|---|---|---|---|
| AdC6 020-HIVgp140-DU172 | yes | stable | yes | correct |
| AdC6 020-HIVgp140-DU422 | yes | stable | yes | correct |
| AdC7 010-HIVgp140-DU172 | yes | stable | yes | correct |
| AdC7 010-HIVgp140-DU422 | yes | stable | yes | correct |
| AdC6 020-SIVgp160 | yes | N.D. | N.D. | correct |
| AdC6 020-HIVgag | yes | N.D. | N.D. | N.D. |
| Ad5 060-HIVgp140-DU422 | yes | stable | yes | correct |
| Ad5 060-SIVgp160 | yes | N.D. | N.D. | N.D. |
| Ad26 011-HIVgp140-DU422 | yes | N.D. | N.D. | correct |

N.D. — Not Determined

The invention claimed is:

1. A replication-incompetent adenovirus vector comprising a deletion in the E3 open reading frame (ORF) of ORF3, ORF4, ORF5, ORF6, and ORF7; and comprising at least one ORF selected from the group consisting of ORF8 and ORF9.

2. The replication-incompetent adenovirus vector of claim 1, which is a human serotype.

3. The replication-incompetent adenovirus vector of claim 1, which has a serotype of a group selected from the group consisting of group A, group B, group C, group D, group E, and group F.

4. The replication-incompetent adenovirus vector of claim 1, which has a serotype selected from the group consisting of Ad2, Ad3, Ad4, Ad5, Ad6, Ad7, Ad11, Ad20, Ad21, Ad22, Ad23, Ad24, Ad25, Ad26, Ad28, Ad34, Ad35, Ad40, Ad41, Ad48, Ad49, and Ad50.

5. The replication-incompetent adenovirus vector of claim 1, which has a serotype selected from the group consisting of Ad C1, Ad C3, Ad C6, Ad C7, and Ad C68.

6. The replication-incompetent adenovirus vector of claim 1, comprising a deletion in E1.

7. An immunogenic composition comprising the replication-incompetent adenovirus vector of claim 1.

8. A dosage unit of the immunogenic composition of claim 7, which comprises $10^8$ to $10^{11}$ adenoviral particles.

9. A method of inducing an immune response to an infectious pathogen in a subject, comprising administering to the subject the immunogenic composition of claim 7.

10. A packaging cell line comprising the replication-incompetent adenovirus vector of claim 1.

11. The packaging cell line of claim 10 comprising HEK293 cells.

12. The replication-incompetent adenovirus vector of claim 1, which has the serotype Ad C7.

13. The replication-incompetent adenovirus vector of claim 1, further comprising all or an antigenic portion of an HIV-1 envelope protein.

* * * * *